(12) United States Patent
Petrillo et al.

(10) Patent No.: US 7,649,178 B2
(45) Date of Patent: Jan. 19, 2010

(54) SOLID STATE DETECTOR PACKAGING TECHNIQUE

(75) Inventors: Michael J. Petrillo, Pleasanton, CA (US); Sorin V. Cora, Anaheim, CA (US); John F. Vesel, Kirtland, OH (US); Sanyi Tseng, San Jose, CA (US); Jinghan Ye, Fremont, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 382 days.

(21) Appl. No.: 11/573,560

(22) PCT Filed: Aug. 2, 2005

(86) PCT No.: PCT/IB2005/052588

§ 371 (c)(1), (2), (4) Date: Feb. 12, 2007

(87) PCT Pub. No.: WO2006/018767

PCT Pub. Date: Feb. 23, 2006

(65) Prior Publication Data
US 2007/0158574 A1    Jul. 12, 2007

Related U.S. Application Data

(60) Provisional application No. 60/601,253, filed on Aug. 13, 2004.

(51) Int. Cl.
*G01T 1/24* (2006.01)
(52) U.S. Cl. .................................. 250/370.09
(58) Field of Classification Search ........... 250/370.01–370.15; 378/98.8, 98.7
See application file for complete search history.

(56) References Cited

U.S. PATENT DOCUMENTS

| 5,464,984 | A | 11/1995 | Cox et al. |
| 6,194,726 | B1 | 2/2001 | Pi et al. |
| 6,555,052 | B2 | 4/2003 | Soga et al. |
| 6,559,451 | B1 * | 5/2003 | Izumi et al. ............ 250/370.08 |

(Continued)

FOREIGN PATENT DOCUMENTS

JP    07333348 A    12/1995

(Continued)

OTHER PUBLICATIONS

McConnell, M. L., et al.; The development of coplanar CZT strip detectors for gamma-ray astronomy; 2001, submitted to proceedings of the GAMMA 2001 High Energy Astrophysics Symposium, 5 pages.

(Continued)

*Primary Examiner*—David P Porta
*Assistant Examiner*—Kiho Kim (57) ABSTRACT

A radiation detector package includes a radiation-sensitive solid-state element (10) having a first electrode (12) and a pixelated second electrode (14) disposed on opposite principal surfaces of the solid-state element. An electronics board (20) receives an electrical signal from the solid-state element responsive to radiation incident upon the radiation-sensitive solid-state element. A light-tight shield (40, 40') shields at least the radiation-sensitive solid-state element from light exposure and compresses an insulating elastomer and metal element connector (30, 32) between the pixelated electrode (14) and contact pads (24) on the electronics board.

23 Claims, 4 Drawing Sheets

U.S. PATENT DOCUMENTS

| | | | |
|---|---|---|---|
| 6,825,472 B2* | 11/2004 | Endo | 250/370.09 |
| 6,963,065 B2* | 11/2005 | Conti et al. | 250/252.1 |
| 2002/0079458 A1* | 6/2002 | Zur | 250/370.11 |
| 2004/0026624 A1 | 2/2004 | Wainer et al. | |
| 2004/0149489 A1 | 8/2004 | Ferrando et al. | |

FOREIGN PATENT DOCUMENTS

| | | |
|---|---|---|
| JP | 11160442 A | 6/1999 |
| JP | 2002181943 A | 6/2002 |
| JP | 2003194951 A | 7/2003 |
| JP | 2004317167 A | 11/2004 |

OTHER PUBLICATIONS

McConnell, M. L., et al.; Three-dimensional imaging and detection efficiency performance of orthogonal coplanar CZT strip detectors; 2000; Proc. SPIE; vol. 4141; pp. 157-167.

Tumer, T. O., et al.; Preliminary results obtained from a novel CdZnTe pad detector and readout ASIC developed for an automatic baggage inspection system; 2001; IEEE Nuclear Science Symposium; vol. 1, pp. 4-36-4-41.

UNH Astrophysics, "Prototype CZT Strip Detector" http://astrophysics.sr.unh.edu/CZT_Prototype.html.

* cited by examiner

SOLID STATE DETECTOR PACKAGING TECHNIQUE

CROSS REFERENCE TO RELATED APPLICATIONS

This application claims the benefit of U.S. provisional application Ser. No. 60/601,253 filed Aug. 13, 2004, which is incorporated herein by reference.

The following relates to the radiation detector arts. It finds particular application in conjunction with radiation detectors for medical imagers employing radiation transmission or radiopharmaceuticals, such as single photon emission computed tomography (SPECT) imagers, positron emission tomography (PET) imagers, transmission computed tomography (CT) imagers, and the like, and will be described with particular reference thereto. However, it finds application in radiation detection generally, and in methods and systems employing radiation detectors, such as radioastronomy, airport luggage screening, planar x-ray imaging in general, and so forth.

In single-photon emission computed tomography (SPECT), a radiopharmaceutical is administered to an imaging subject, and one or more radiation detectors, commonly called gamma cameras, are used to detect the radiopharmaceutical via radiation emission caused by radioactive decay events. Typically, each gamma camera includes a radiation detector array and a honeycomb collimator disposed in front of the radiation detector array. The honeycomb collimator defines a linear or small-angle conical line of sight so that the detected radiation comprises projection data. If the gamma cameras are moved over a range of angular views, for example over a 180° or 360° angular range, then the resulting projection data can be reconstructed using filtered backprojection or another imaging technique into an image of the radiopharmaceutical distribution in the imaging subject. Advantageously, the radiopharmaceutical can be designed to concentrate in selected tissues, such as the kidneys, to provide preferential imaging of those selected tissues.

In positron emission tomography (PET), a radiopharmaceutical is administered to the imaging subject, in which the radioactive decay events of the radiopharmaceutical produce positrons. Each positron interacts with an electron to produce a positron-electron annihilation event that emits two oppositely directed gamma rays. Using coincidence detection circuitry, a ring array of radiation detectors surrounding the imaging subject detect the simultaneous oppositely directed gamma ray events corresponding to the positron-electron annihilation. A line of reaction connecting the two simultaneous detections contains the position of the positron-electron annihilation event. Such lines of reaction are analogous to projection data and can be reconstructed to produce a two- or three-dimensional image.

In a planar x-ray imaging, a radiation source irradiates an imaging subject, and a radiation detector array disposed on the opposite side of the imaging subject detects the transmitted radiation. Due to attenuation of radiation by tissues in the imaging subject, the detected radiation provides a two-dimensional planar representation of bones or other hard, radiation-absorbing structures in the imaging subject. Such transmission-based imaging is improved upon in transmission computed tomography imaging, in which the x-ray tube or other radiation source is revolved around the imaging subject to provide transmission views or projection data over an extended angular range, for example over a 180° or 360° span of angular views. Using filtered backprojection or another image reconstruction technique, this radiation projection data is reconstructed into a two- or three-dimensional image representation.

All of these techniques and other radiation-based medical imaging techniques share a common need for compact and robust radiation detector packages. Such radiation detector packages are also used in other areas, such as in radioastronomy and airport luggage scanning. In the past, SPECT and PET radiation detector packages have typically included photomultiplier tubes optically coupled with scintillator crystals. Absorption of a radiation particle by the scintillator crystal produces a scintillation of light which is measured by the photomultiplier tubes. Such scintillator/photomultiplier tube radiation detectors are complex, expensive to manufacture, and fragile.

In another approach, an electrically biased solid-state radiation detector is employed. A radiation-sensitive solid-state film or block of material, such as cadmium zinc telluride (CZT), is biased by an anode and a cathode disposed on opposite sides of the film or block to produce an electric field in the material. Absorption of a radiation particle by the solid state material creates a plasma of electrons and holes, which the electric field separates. The holes go to the cathode while the electrons go the anode, thus producing an electric detector current. Typically, either the anode or the cathode is pixelated to enable the location of the radiation absorption event on the face of the radiation detector to be spatially resolved. A printed circuit board having an array of electrical pads corresponding to the pixels of the pixelated electrode is secured to the radiation-sensitive solid-state material with the electrode pixels and the electrical pads aligned and in contact with one another. Electronic components disposed below the electrical pads receive and process the detector signals.

Existing solid state radiation detector packages have certain disadvantages. They typically include a direct physical connection between the radiation-sensitive solid-state material and the printed circuit board. This arrangement is susceptible to reliability problems due to mechanical stresses or shocks, or due to thermal stresses produced by differential thermal expansion of the solid-state material and the printed circuit board. Moreover, existing solid state radiation detector packages are typically problematic from a thermal heat sinking standpoint, because the solid-state material is substantially thermally isolated, and because some designs include multiple layers of electronics which increases the thermal resistance of heat removal paths. In addition to producing undesirable heat retention, the relatively thermally isolated nature of the radiation-sensitive solid-state material in typical existing solid state radiation detector packages makes it difficult to uniformly cool the solid-state material to produce a uniform dark current across the radiation detector area.

The following contemplates improved apparatuses and methods that overcome the aforementioned limitations and others.

According to one aspect, a radiation detector package is disclosed, including a radiation-sensing solid-state element. A first electrode is disposed on a first principal surface of the solid-state element. A pixelated second electrode is disposed on a second principal surface of the solid-state element opposite the first principal surface. An electronics board receives an electrical signal from the solid-state element responsive to radiation incident upon the radiation-sensitive solid-state element. A light-tight shield is provided that shields at least the radiation-sensitive solid-state element from light exposure and compressively maintains the radiation-receiving element and the electronics board in a preselected, electrically interconnected relationship.

According to another aspect, a method of making a radiation detector package is disclosed. A radiation-sensing solid-state element with a first electrode on a first principal surface and a second, pixilated electrode on a second, opposite principal surface, an electronics board with an array of electrical contact pads facing the pixilated electrode, and an electrically conductive membrane are staked with the electrically conductive membrane between the pixilated electrode and the electrical contract pads. The electrically conductive membrane is compressed into electrical and mechanical contact with the pixilated electrode and the electrical contact pads with a light-tight shield that shields the radiation-receiving element from light.

One advantage resides in simplified radiation detector packaging with less stringent tolerances for alignment of components.

Another advantage resides in improved robustness against mechanical stresses and shocks and against thermal heating and cooling stresses.

Another advantage resides in improved heat sinking of the radiation detector.

Yet another advantage resides in improved thermal uniformity in active cooling of the radiation detector.

Still yet another advantage resides in providing tillable detectors with backside electrical connections for constructing radiation detector arrays of arbitrary size.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

With reference to FIGS. 1-5, a radiation detector package 8 includes radiation-sensitive solid-state element 10 which in the illustrated embodiment is a cadmium zinc telluride (CZT) block. Other radiation-sensitive materials such as cadmium telluride (CdTe) or mercury iodide (HgI), for example, can also be used as the solid state element. A cathode 12 is disposed on a radiation-receiving principal side of the radiation-sensitive solid-state element 10, and a pixelated anode 14 is disposed on a second principal side or backside of the radiation-sensitive solid-state element 10 opposite the radiation-receiving side. In operation, a negative bias is applied to the cathode 12 relative to the pixelated anode 14. When a radiation particle is absorbed by the radiation-sensitive solid-state element 10, an electron-hole pair plasma is generated, and the electrons and holes are swept to the anode 14 and cathode 12, respectively, to generate a detector current indicative of the radiation particle. By pixilating the anode 14, the radiation particle absorption event can be spatially localized on the face of the detector based on which anode pixel or small plurality of anode pixels conduct the detector current. Instead of the illustrated continuous cathode 12 and pixelated anode 14, a continuous anode and pixelated cathode can be used for spatial localization with a suitable change in orientation and biasing of the solid state element.

Figure 1:
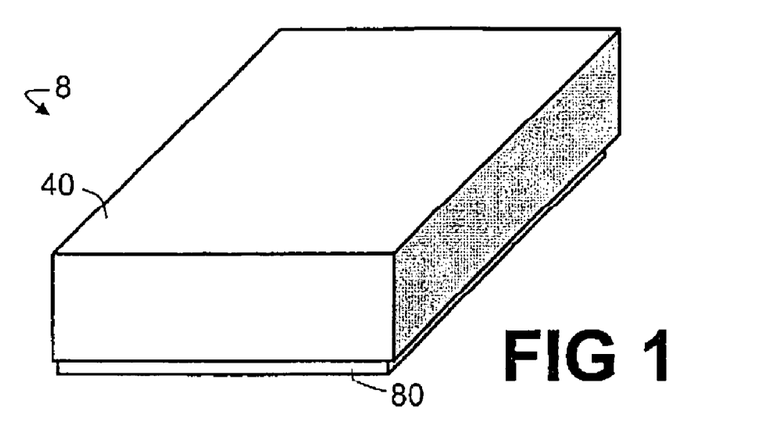
FIG. 1 shows a perspective view of a solid state radiation detector package.
Figure 2:
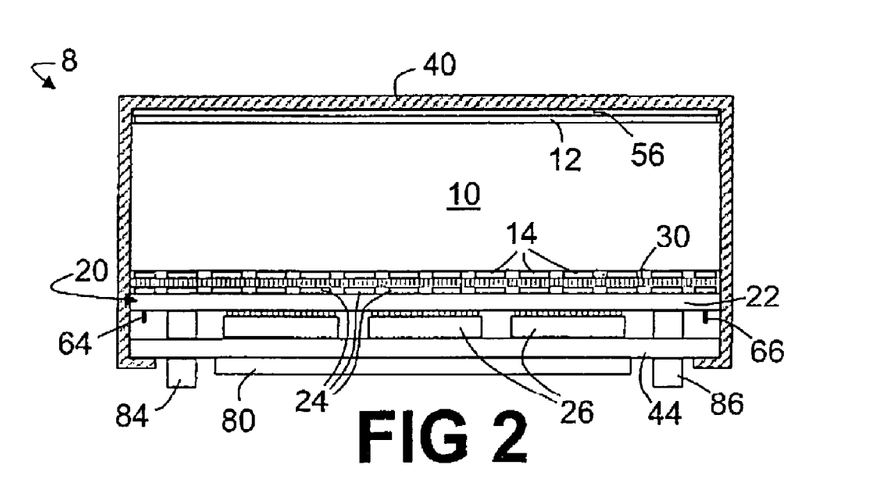
FIG. 2 shows a side view of the radiation detector package of FIG. 1 with one side of the light-tight shield removed to reveal internal components of the package.
Figure 4:
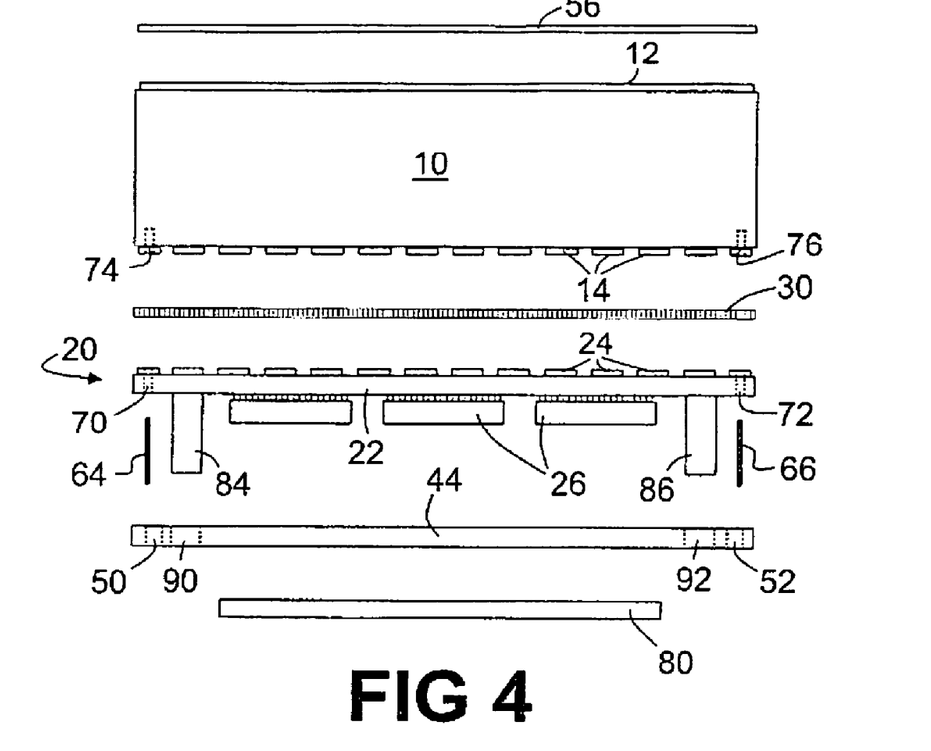
FIG. 4 shows an exploded side view of the radiation detector package of FIG. 1 with the light-tight shield removed.
Figure 5:
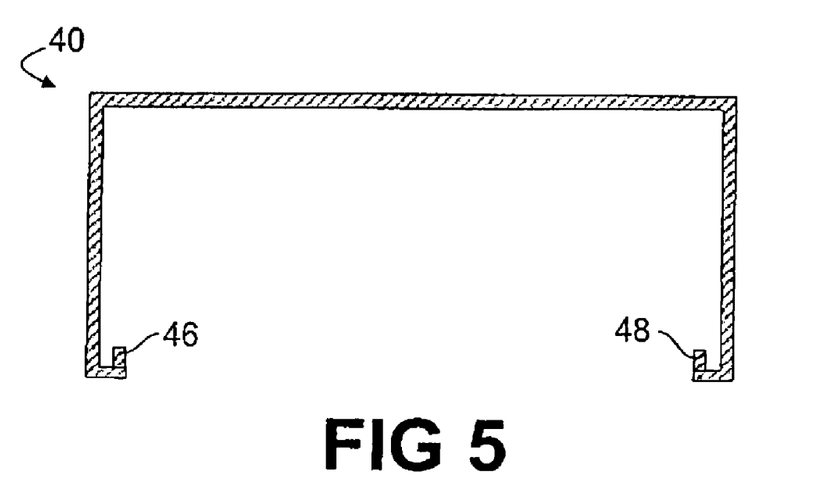
FIG. 5 shows a side sectional view of the light-tight shield including the sealing lip.

An electronics board 20 receives the detector signal. The electronics board includes a printed circuit board 22 including an array of electrical contact pads 24 disposed on a first principal side facing the solid state element 10, and one or more integrated circuit components 26 or other electronic components disposed on a second principal side opposite the first principal side and distal from the solid state element 10. The one or more integrated circuit components 26 are connected with the array of electrical pads 24 by printed circuitry of the printed circuit board 22. In some embodiments, the integrated circuit components 26 include one or more application-specific integrated circuits (ASIC's) performing detector signal pre-amplification, signal digitization, or other signal processing. In other embodiments, the integrated circuit components 26 include one or more microcontrollers, microprocessors, field-programmable gate arrays (FPGA's), or other programmable digital components for processing digitized detector signals. Discrete circuit components such as discrete resistors or transistors can also be disposed on the second principal side of the printed circuit board 22.

The elements of the array of electrical pads 24 correspond with the pixels of the pixelated anode 14. To electrically connect the pixels of the pixelated anode 14 with the corresponding elements of the array of electrical pads 24 in a robust manner that is resistant to mechanical stresses produced by heating, cooling, gantry rotation, or the like, at least one electrically conductive elastic membrane 30, 32 or other compressible connector is disposed between the pixelated anode 14 and the array of electrical pads 24 of the electronics board 20.

In some embodiments the connector is an electrically conductive fiber-based compressible or elastic membrane 30 that includes a plurality of metal fibers or other electrically conductive fibers dispersed in a deformable membrane with the electrically conductive fibers oriented generally transverse to the plane of the elastic membrane, i.e., vertical in the orientation of FIG. 4. The electrically conductive fibers are thin enough to flex in compression, yet stiff enough to bias themselves to maintain contact with pads on the anode and circuit board. The insulating, compressible material is thick enough that adjacent fibers do not connect electrically.

Figure 3:
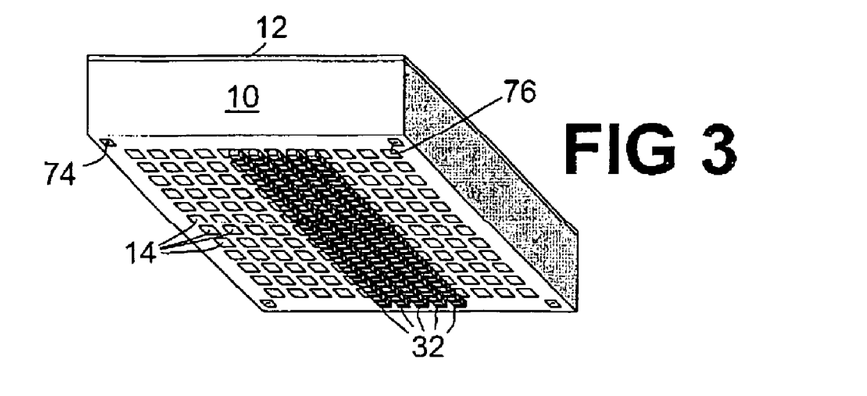
FIG. 3 shows a perspective view of the radiation-sensitive solid-state element of the radiation detector package of FIG. 1, including the pixelated anode.

In other embodiments the elastic membrane is a plurality of zebra elastomeric connector strips 32 each including linearly alternating electrically conductive and electrically insulative portions. Such zebra elastomeric connector strips 32 are illustrated in FIG. 3. In FIG. 3, only five zebra elastomeric connector strips 32 are illustrated in order to show the pixelated anode 14; however, there would in general be enough zebra elastomeric connector strips 32 to connect all the pixels of the pixelated anode 14 with corresponding electrical pads of the array of electrical pads 24.

The fiber-based electrically conductive elastic membrane 30 should employ electrically conductive fibers having diameters and lateral fiber separations which are substantially smaller than the size and spacing of the pixels of the pixelated anode 14, and the fibers should be generally electrically isolated from one another. In this manner, the fiber-based electrically conductive elastic membrane 30 conducts electrical current in the direction transverse to the membrane 30, but does not conduct electrical current along the membrane 30. Hence, a detector current generated in one pixel of the pixelated anode 14 is communicated to the corresponding electrical pad of the array of electrical pads 24 without cross-talk due to lateral conduction of electrical current.

Similarly, the zebra elastomeric connectors 32 should be spaced apart from one another to prevent electrical conduction therebetween. Optionally, the zebra elastomeric connectors 32 can include insulative sidewalls to prevent electrical cross-talk between neighboring zebra elastomeric connectors 32. The pitch or period of the alternating electrically conductive and electrically insulative portions should be much smaller than the size and spacing of the pixels of the pixelated anode 14 to avoid cross-talk between neighboring pixels of the pixelated anode 14 along the zebra elastomeric connector 32. In some embodiments, the width of the zebra elastomeric connectors 32 is substantially less than the pixel size to prevent shorting across pixels. In other embodiments, there is one zebra elastomeric connector 32 for each corresponding row of pixels of the pixelated anode 14, and the width of each zebra elastomeric connector 32 comports with the width of one row of anode pixels.

The illustrated electrically conductive elastic membranes 30, 32 are examples. Those skilled in the art can readily construct similar electrically conductive elastic membranes having substantial electrical conductivity transverse to the membrane without substantial lateral electrical conductivity along the membrane. Substantially any electrically conductive elastic membrane having such anisotropic electrical conductivity characteristics can be used to connect the pixelated anode 14 and the array of electrical pads 24 in a mechanically and thermally robust manner. Moreover, the electrically conductive portions are typically thermally conductive and the electrically insulating portions can be thermally insulating or conductive to control heat transfer between the solid-state element 10 and the electronics board 20.

The use of the at least one electrically conductive elastic membrane 30, 32 provides a number of advantages. The elastomer provides an elastic cushion to accommodate mechanical or thermal stresses. The electrically conductive elastic membrane 30, 32 also reduces the tolerances required in aligning the pixels of the pixelated anode 14 with the electrical pads of the array of electrical pads 24.

Together with these advantageous mechanical properties, if the one or more elastic membranes 30, 32 are thermally conductive, then they can provide a large-area thermal connection between the radiation-sensitive solid-state element 10 and the electronics board 20, which spans the active area of the radiation detector. This large-area thermal connection enhances thermal uniformity across the detector area for heat sinking or active cooling. In some embodiments, however, it is contemplated to use a thermally insulating elastic membrane. For example, if the one or more integrated circuit components 26 produce a large quantity of heat, it may be advantageous to use a thermally insulating elastic membrane to thermally isolate the radiation-sensitive solid-state element 10 from the electronics board 20.

A light-tight shield 40 shields the radiation-sensitive solid-state element 10 from exposure to light or other electromagnetic radiation having substantially lower energies than the radiation intended to be detected. Such shielding reduces dark currents in the radiation-sensitive solid-state element 10. The illustrated light-tight shield 40 includes a front principal side disposed over the light-receiving principal side of the radiation-sensitive solid-state element 10 (that is, the side on which the cathode 12 is disposed) and a plurality of sidewalls extending from edges of the front principal side across sidewalls of the solid-state element 10 and electronics board 20. The sidewalls of the light-tight shield 40 connect with a thermally conductive plate 44 disposed on the second principal side of the electronics board 20 distal from the radiation-sensitive solid-state element 10. The thermally conductive plate 44 is disposed on the backside of the radiation detector package 8. In the illustrated embodiment, the light-tight shield 40 includes a lip 46, 48 (labeled in FIG. 5) that mates with a slots 50, 52 of the thermally conductive plate 44 (slots shown in phantom in FIG. 4). Other coupling arrangements can be used. The light-tight shield 40 and the thermally conductive plate 44 together define a housing containing the radiation-sensitive solid-state element 10, the electronics board 20, and the electrically conductive elastic membrane 30, 32.

The radiation-sensitive solid-state element 10, the electronics board 20, and the electrically conductive elastic membrane 30, 32 are compressively held between the connected light-tight shield 40 and the thermally conductive plate 44. The compression facilitates thermal contact between the thermally conductive plate 44 and the one or more integrated circuit components 26, and also facilitates electrical connection between the pixelated anode 14 and the array of electrical pads 24 via the electrically conductive elastic membrane 30, 32. An insulating isolation sheet or membrane 56 is disposed between the cathode 12 and the light-tight shield 40 to provide electrical isolation therebetween.

The compression provided by the light-tight shield 40 and the thermally conductive plate 44 holds the radiation-sensitive solid-state element 10 and the electronics board 20 together. To align the pixelated anode 14 of the radiation-sensitive solid-state element 10 and the array of electrical pads 24 of the electronics board 20, a plurality of alignment pins 64, 66 pass through alignment holes 70, 72 of the electronics board 20 (shown in phantom in FIG. 4), through corresponding alignment holes 74, 76 of the radiation-sensitive solid-state element 10 (shown in FIG. 3 and in phantom in FIG. 4). Optionally, a heat sinking element 80 is disposed on the backside of the radiation detector package 8 in contact with the thermally conductive plate 44. For example, the heat sinking element 80 can be a Peltier board or device.

In some embodiments, the radiation detector package 8 is actively cooled by the Peltier board 80, a surrounding liquid coolant flow or immersion, or so forth. When the package 8 is cooled below the dew point such that water would normally condense inside of the package 8, it is advantageous to eliminate water vapor from inside of the package 8. Toward that end, the connection between the light-tight shield 40 and thermally conductive plate 44 is optionally a hermetic seal, achieved for example by applying an epoxy or other sealant at the connection of the lip 46, 48 of the shield 40 and the slots 50, 52 of the plate 44. By fabricating the radiation detector package 8 in a dry nitrogen or other low moisture environment, and then hermetically sealing the housing in the low moisture environment, water condensation within the package 8 is reduced or avoided. Alternatively, the radiation detector package 8 can be fabricated in moisture-containing air up to and including hermetic sealing together of the shield 40 and plate 44, followed by backfilling of the housing by dry nitrogen or another inert gas through suitable openings (not shown) in the shield 40 or plate 44 (or through a gap therebetween intentionally left during the hermetic sealing), finally followed by hermetic sealing of the backfilling openings by an epoxy or the like.

The radiation detector package 8 has sides that are buttable with other detector packages to define large area radiation detector arrays. One or more backside electrical connectors 84, 86 are disposed on the same side of the electronics board 20 as the one or more integrated circuit components 26. The backside electrical connectors 84, 86 pass through openings 90, 92 in the thermally conductive plate 44 (shown in phantom in FIG. 4) to provide external electrical accessibility. By placing the electrical connectors 84, 86 on the backside of the radiation detector package 8, the sides of the package 8 are unimpeded and can abut sides of another similar radiation detector package 8. This enables a plurality of the radiation detector packages 8 to be tiled to form a larger-area radiation detector array.

Figure 6:
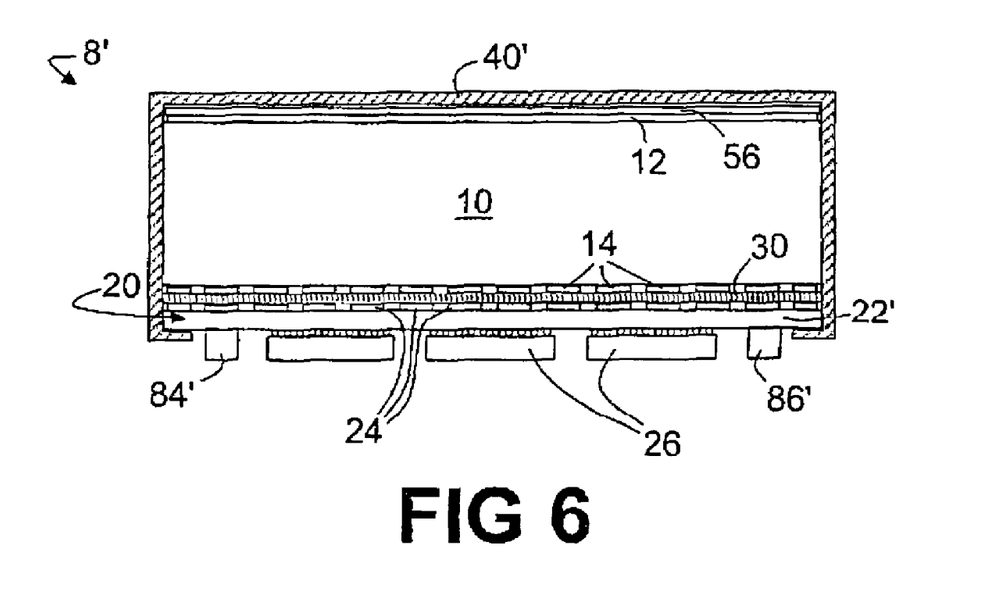
FIG. 6 shows a side view of a second radiation detector package with one side of the light-tight shield removed to reveal internal components of the second radiation detector package.

With reference to FIG. 6, another radiation detector package 8' includes the radiation-sensitive solid-state element 10 with cathode 12 and pixelated anode 14 electrically coupled with the array of electrical pads 24 of the electronics board 20 via the electrically conductive elastic membrane 30, 32, as in the detector package 8. However, the radiation detector package 8' omits the thermally conductive plate 44. A light-tight shield 40' similar to the light-tight shield 40 of the package 8 couples instead with a circuit board 22' that is similar to the circuit board 22, optionally modified by including slots (not shown) for receiving the lip of the light-tight shield 40'. Since the thermally conductive plate 44 is omitted, shorter backside electrical connectors 84', 86' can be employed in the radiation detector package 8'.

The radiation detectors 8, 8' or their equivalents can be employed in substantially any type of application that calls for detecting radiation. For example, the radiation detectors 8, 8' or their equivalents can serve as radiation detectors in a transmission computed tomography imager, a single-photon computed tomography (SPECT) imager, a positron emission tomography (PET) imager, a planar x-ray system, a radiotelescope, an airport luggage scanning system, or so forth.

Figure 7:
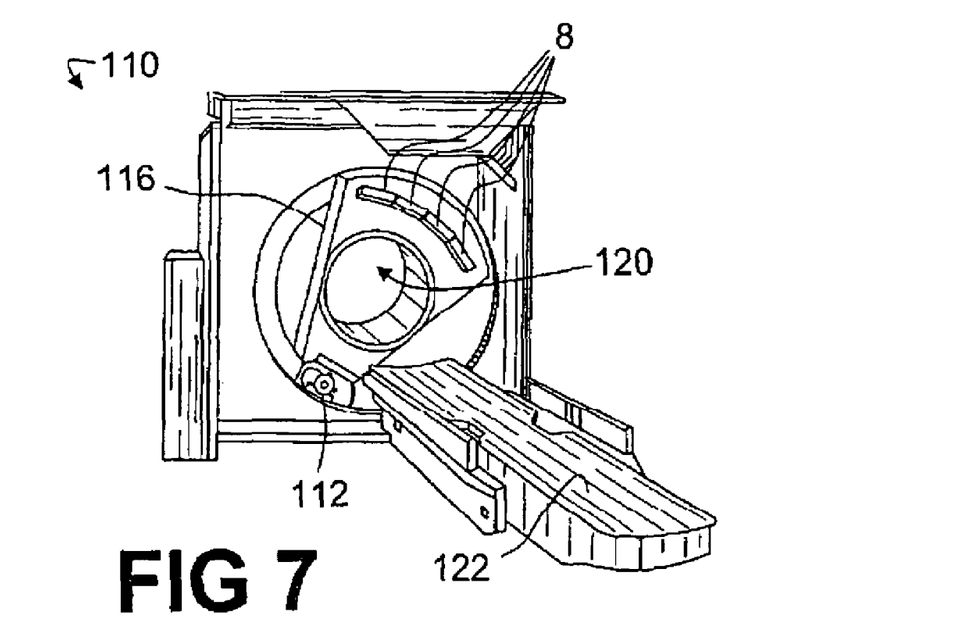
FIG. 7 shows a transmission computed tomography scanner employing an abutting plurality of the radiation detector packages of FIG. 1 as an arced radiation detector array.

With reference to FIG. 7, a transmission computed tomography imaging scanner 110 includes an x-ray tube 112 and a two-dimensional radiation detector array constructed of tiled radiation detector packages 8 mounted on a rotating gantry 116 on opposite sides of an imaging region 120. (The x-ray tube 112, radiation detector packages 8, and rotating gantry 116 are exposed in FIG. 7 for expository purposes; however, it will be appreciated that typically these components are enclosed in a stationary gantry housing). An imaging subject (not shown) is disposed on a patient support 122 and moved into the imaging region 120 for computed tomography imaging. It will be noted that adjacent radiation detector packages 8 in the scanner 110 are arranged tilted with respect to one another to define an arced detector having a curvature that substantially comports with a fan-, wedge-, or cone-beam of x-rays produced by the x-ray tube 112.

Figure 8:
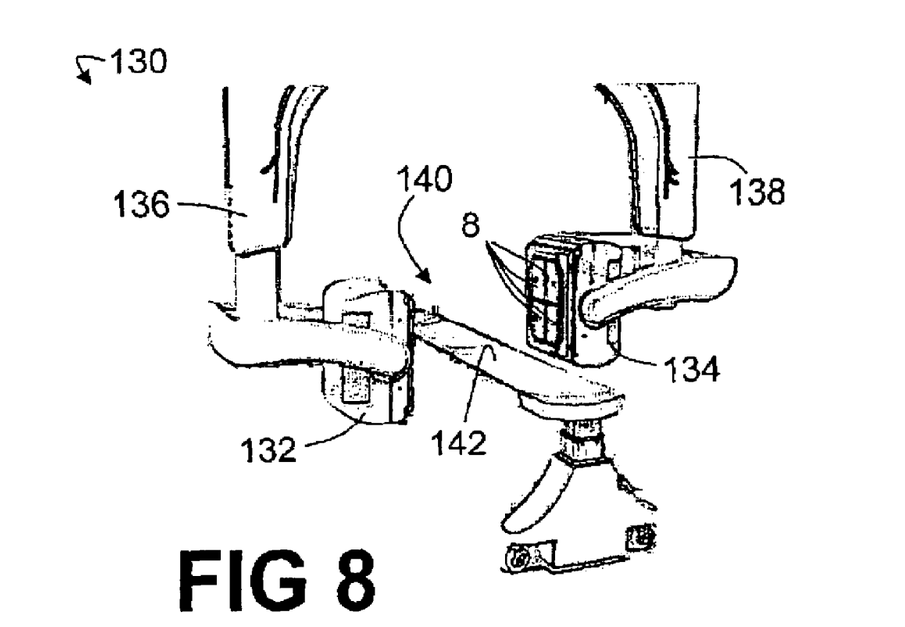
FIG. 8 shows a single photon emission computed tomography (SPECT) scanner with two heads each employing an abutting plurality of the radiation detector packages of FIG. 1 as a radiation detector array.

With reference to FIG. 8, a single photon emission computed tomography (SPECT) scanner 130 includes a plurality of gamma detector heads 132, 134 arranged on robotic gantry arms 136, 138 to view an imaging region 140. Each gamma camera 132, 134 includes an array of radiation detector packages 8. Typically, a honeycomb, parallel-hole, slat, pin hole, diverging, converging, or other type of collimator (not shown) is disposed in front of the radiation detector packages 8 to define linear or small-angle conical lines-of-sight or other suitable views for each pixel. An imaging subject (not shown) is disposed on a patient support 142 and moved into the imaging region 140 for computed tomography imaging. The radioactivity dose of the radiopharmaceutical is typically low so as not to injure the imaging subject. Accordingly, the gamma cameras 132, 134 are advantageously mounted on the robotic gantry arms 136, 138 rather than on a rotating gantry, and the arms 136, 138 move the cameras 132, 134 conformally with the outer shape of the imaging subject to minimize camera-to-subject distance and thus maximize the detected radiation intensity.

The computed tomography scanner 110 of FIG. 7 includes the x-ray tube 112 which typically generates a relatively high flux of lower energy x-rays. Accordingly, the radiation detector packages 8 in the computed tomography scanner 110 suitably employ a relatively thin radiation-sensitive solid-state element 10, for example a 2 millimeter thick CZT film or block. Due to the high levels of radiation produced by the x-ray tube 112, it is contemplated to include a ground plane (not shown) containing a radiation-absorptive high-Z material in the printed circuit board 22 of the radiation detector packages 8 to reduce the radiation exposure of the underlying one or more integrated circuit components 26.

In contrast, the gamma cameras 132, 134 of the SPECT scanner 130 of FIG. 8 typically receive a relatively lower flux of higher energy radiation due to a relatively low concentration of radiopharmaceutical administered to the imaging subject. Accordingly, the radiation detector packages 8 in the SPECT scanner 130 typically employ a relatively thicker radiation-sensitive solid-state element 10 due to the higher energy radiation, for example a 5-10 millimeter thick CZT film or block. More generally, the thickness of the radiation-sensitive solid-state element 10 is selected based on the radiation-stopping efficiency of the material, the energy (e.g., keV) of the particles, and similar considerations.

While two example medical imaging scanners 110, 130 have been illustrated, it will be appreciated that the radiation detectors 8, 8' are readily employed in other radiation-based medical imagers, such as positron emission tomography (PET) scanners and planar x-ray imagers. Moreover, the radiation detectors 8, 8' are readily employed in other applications such as radioastronomy and airport luggage scanning.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A radiation detector package comprising:
   a radiation sensing solid state element;
   a first electrode disposed on a first principal surface of the solid state element;
   a pixelated second electrode disposed on a second principal surface of the solid state element opposite the first principal surface;
   an electronics board receiving an electrical signal from the solid state element responsive to radiation incident upon the radiation sensitive solid state element;
   a light tight shield shielding at least the radiation sensitive solid state element from light exposure and compressively maintaining the radiation-sensing element and the electronics based in a preselected, electrically interconnected relationship; and
   at least one electrically conductive membrane disposed between the pixelated second electrode and the electronics board, the electrically conductive membrane providing electrical connection between pixels of the pixelated second electrode and corresponding electrical pads of the electronics board; and a thermally conductive plate in thermal communication with elements of the electronics board, the light tight shield and the thermally conductive plate being connected together, the radiation sensitive solid state element, electronics board, and electrically conductive membrane being compressively held between the connected thermally conductive plate and light tight shield.

2. The radiation detector package as set forth in claim 1, wherein the connection between the light tight shield and the thermally conductive plate hermetically seals the radiation sensitive solid state element, electronics board, and electrically conductive elastic membrane inside of a housing defined by the light tight shield and thermally conductive plate and further including a dry atmosphere inside the housing.

3. A radiation detector package comprising:
a radiation sensing solid state element;
a first electrode disposed on a first principal surface of the solid state element;
a pixelated second electrode disposed on a second principal surface of the solid state element opposite the first principal surface;
an electronics board receiving an electrical signal from the solid state element responsive to radiation incident upon the radiation sensitive solid state element;
a light tight shield shielding at least the radiation sensitive solid state element from light exposure and compressively maintaining the radiation-sensing element and the electronics based in a preselected, electrically interconnected relationship, the light tight shield including a front principal side disposed over the radiation sensitive solid state element and a plurality of sidewalls extending from edges of the front principal side across sidewalls of the solid state element and electronics board, the sidewalls connecting with one of (i) the electronics board and (ii) a thermally conductive plate disposed on a side of the electronics board distal from the radiation sensitive solid state element; and
at least one electrically conductive membrane disposed between the pixelated second electrode and the electronics board, the electrically conductive membrane providing electrical connection between pixels of the pixelated second electrode and corresponding electrical pads of the electronics board.

4. The radiation detector package as set forth in claim 3, further including:
an insulating layer disposed between the light-tight shield and the first electrode.

5. The radiation detector package as set forth in claim 3, wherein the electronics board includes:
a printed circuit board, the electrical pads of the electronics board being disposed on a first principal side of the printed circuit board; and
one or more integrated circuit components disposed on a second principal side of the electronics board opposite the first principal side of the printed circuit board, the one or more integrated circuit components being electrically connected with the electrical pads on the first principal side by printed circuitry of the printed circuit board.

6. The radiation detector package as set forth in claim 5, further includes:
a thermally conductive plate abutting the integrated circuit components, the light-tight shield being deformed around the thermally conductive plate compressively gripping the electrically conductive membrane between the pixelated second electrode and the pads.

7. The radiation detector package as set forth in claim 3, wherein the radiation sensitive solid state element is a CZT crystal.

8. A radiation detector package comprising:
a radiation sensing solid state element;
a first electrode disposed on a first principal surface of the solid state element;
a pixelated second electrode disposed on a second principal surface of the solid state element opposite the first principal surface;
an electronics board receiving an electrical signal from the solid state element responsive to radiation incident upon the radiation sensitive solid state element;
a light tight shield shielding at least the radiation sensitive solid state element from light exposure and compressively maintaining the radiation-sensing element and the electronics based in a preselected, electrically interconnected relationship; and
at least one electrically conductive membrane disposed between the pixelated second electrode and the electronics board, the electrically conductive membrane providing electrical connection between pixels of the pixelated second electrode and corresponding electrical pads of the electronics board;
wherein the electronics board includes:
a printed circuit board, the electrical pads of the electronics board being disposed on a first principal side of the printed circuit board,
one or more integrated circuit components disposed on a second principal side of the electronics board opposite the first principal side of the printed circuit board, the one or more integrated circuit components being electrically connected with the electrical pads on the first principal side by printed circuitry of the printed circuit board, and
one or more electrical connectors disposed on the second principal side of the printed circuit board such that the radiation detector package has a radiation sensitive first principal package side, a second principal package side opposite the first principal package side with the one or more electrical connectors, and a plurality of package sidewalls extending between the first and second principal sides, the sidewalls being buttable with sidewalls of other radiation detector packages to enable tiling of a plurality of radiation detector packages as a radiation detector array.

9. The radiation detector package as set forth in claim 8, wherein the light tight shield and the electronics board are connected together, the radiation sensitive solid state element and the electrically conductive elastic membrane being compressively held between the connected light tight shield and electronics board.

10. A method of making a radiation detector package comprising:
stacking (i) a radiation-sensing solid-state element with a first electrode on a first principal surface and a second pixelated electrode on a second, opposite principle surface, (ii) an electronics board with an array of electrical contact pads facing the pixelated electrode, (iii) an electrically conductive membrane between the pixelated electrode and the electrical contact pads, and (iv) a cold plate on an opposite side of the electronics board from the radiation sensing element; and compressing the electrically conductive membrane into electrical and mechanical contact with the pixelated electrode and the electrical contact pads with a light-tight shield that shields the radiation receiving element from light, the compressing including bending the light-tight shield around the cold plate.

11. The method according to claim 10, wherein the light-tight shield is hermetically sealed to the cold plate and further including:
before the compressing step, filling the package with dry gas.

12. A radiation detector package made according to the method of claim 10.

13. A method of medical imaging comprising:
sensing radiation exiting a patient with the detector package of claim 12;
reconstructing a medical diagnostic image from the sensed radiation.

14. An imaging detector comprising:
a radiation-sensing solid-state element;
a first electrode disposed on a first surface of the solid-state element;
a pixelated second electrode disposed on a second surface of the solid-state element;
an electronics board receiving an electrical signal from the solid-state element responsive to radiation incident upon the solid state element; and
at least one electrically conductive membrane disposed between the pixelated second electrode and the electronics board, the electrically conductive membrane providing electrical connection between the pixels of the pixelated second electrode and selected portions of the electronics board, the at least one electrically conductive membrane comprising at least one of: (i) an elastic membrane and (ii) an electrically conductive membrane having anisotropic electrical conductivity transverse to the membrane without substantial lateral electrical conductivity along the membrane.

15. The imaging detector of claim 14 wherein the at least one electrically conductive membrane disposed between the pixelated second electrode and the electronics board is an elastic membrane.

16. The imaging detector of claim 14 wherein the at least one electrically conductive membrane disposed between the pixelated second electrode and the electronics board has anisotropic electrical conductivity transverse to the membrane without substantial lateral electrical conductivity along the membrane.

17. An imaging detector comprising:
a radiation-sensing solid-state element;
a first electrode disposed on a first surface of the solid-state element;
a pixelated second electrode disposed on a second surface of the solid-state element;
an electronics board receiving an electrical signal from the solid-state element responsive to radiation incident upon the solid state element; and
at least one electrically conductive membrane disposed between the pixelated second electrode and the electronics board, the electrically conductive membrane providing electrical connection between the pixels of the pixelated second electrode and selected portions of the electronics board, the electrically conductive membrane being compressively held between pixelated second electrode and the electronics board.

18. A medical imager selected from a group consisting of: (i) a single photon emission computed tomography (SPECT) imager, (ii) a positron emission tomography (PET) imager, and (iii) a transmission computed tomography imager, the medical imager employing an imaging detector as set forth in claim 17.

19. The imaging detector of claim 17 further comprising a housing shielding at least a portion of the solid-state element from light exposure.

20. The imaging detector of claim 19 wherein the housing provides compressive force that acts upon the electrically conductive membrane.

21. A radiation detector package comprising:
a radiation sensing solid state element;
a first electrode disposed on a first principal surface of the solid state element;
a pixelated second electrode disposed on a second principal surface of the solid state element opposite the first principal surface;
an electronics board receiving an electrical signal from the solid state element responsive to radiation incident upon the radiation sensitive solid state element;
a light tight shield shielding at least the radiation sensitive solid state element from light exposure and compressively maintaining the radiation-sensing element and the electronics based in a preselected, electrically interconnected relationship; and
at least one electrically conductive membrane disposed between the pixelated second electrode and the electronics board, the electrically conductive membrane providing electrical connection between pixels of the pixelated second electrode and corresponding electrical pads of the electronics board, wherein the at least one electrically conductive membrane disposed between the pixelated second electrode and the electronics board is an elastic membrane having anisotropic electrical conductivity transverse to the membrane without substantial lateral electrical conductivity along the membrane.

22. The radiation detector package as set forth in claim 21, wherein the electrically conductive membrane includes:
an electrically insulating elastic membrane with spaced, flexible, electrically conductive elements dispersed therein, the electrically conductive elements being oriented generally transverse to the plane of the electrically insulating elastic membrane.

23. The radiation detector package as set forth in claim 22, wherein the electrically conductive elements are fibers.

* * * * *